United States Patent [19]
Marchal et al.

[11] Patent Number: 5,900,366
[45] Date of Patent: May 4, 1999

[54] PRODUCTION OF SOPHOROLIPID ACETATE ACIDS FROM OILS OR ESTERS

[75] Inventors: Rémy Marchal, Chatou; Jeannine Lemal, Rueil-Malmaison; Caroline Sulzer, Rueil-Malmaison; Anne-Marie Davila, Rueil-Malmaison, all of France

[73] Assignee: Institut Français Du Pétrole, Rueil-Malmaison Cedex, France

[21] Appl. No.: 08/078,091

[22] Filed: Jun. 18, 1993

[30] Foreign Application Priority Data

Jun. 18, 1992 [FR] France .................................. 92/07.407

[51] Int. Cl.$^6$ .............................. C12P 17/12; C12P 17/02
[52] U.S. Cl. ...................... 435/123; 435/124; 435/134; 435/137; 435/171; 435/72; 435/249; 435/255.4
[58] Field of Search ..................................... 435/123, 124, 435/134, 137, 171, 249, 255.4, 72

[56] References Cited

U.S. PATENT DOCUMENTS

| | | |
|---|---|---|
| 3,205,150 | 9/1965 | Spencer et al. . |
| 3,312,684 | 4/1967 | Spencer et al. . |
| 3,445,337 | 5/1969 | Spencer et al. . |
| 3,622,344 | 11/1971 | Allingham ............................... 435/243 |
| 4,753,885 | 6/1988 | Dietsche et al. ......................... 435/243 |

OTHER PUBLICATIONS

Hans–Joachim Asmer et al., "Microbial Production, Structure Elucidation, and Bioconversion of Sophorose Lipids," *Journal of the American Oil Chemists' Society*, vol. 65, No. 9, Sep. 1988, pp. 1460–1466.

Primary Examiner—Leon B. Lankford, Jr.
Attorney, Agent, or Firm—Millen, White, Zelano & Branigan

[57] ABSTRACT

A process for the fed batch production of a sophorolipid composition is described, in which culturing takes place of at least one *Candida bombicola* strain in a culture medium incorporating a sugar and a nitrogen source and said cultured strain is exposed in a reaction zone to a supply of an appropriate substrate under adequate aeration, temperature and pH conditions and at least once the following sequence is performed: a) the strain is continuously supplied with substrate at a supply rate in the reaction zone between 0.01 and 4 grams per hour and per liter of initial reaction volume and for a supply time such that the residual substrate concentration in the reaction zone is maintained at a value at the most equal to 18 grams per liter of initial reaction volume during said supply time; and b) the sophorolipid composition produced is recovered; the process being characterized in that the substrate essentially consists of at least one animal oil, at least one vegetable and/or at least one ester of said oil, said oils and said ester incorporating an aliphatic linear chain with 10 to 24 carbon atoms.

18 Claims, No Drawings

PRODUCTION OF SOPHOROLIPID ACETATE ACIDS FROM OILS OR ESTERS

BACKGROUND OF THE INVENTION

The invention relates to a process for the production with continuous supply or fed batch of a sophorolipid composition, incorporating a major part of at least partly acetylated acids and the thus obtained sophorolipid composition.

It is stated in U.S. Pat. Nos. 3,205,150 and 3,312,684 that a quantity of sophorolipids was produced by a fermentation process using a culture of *Torulopsis bombicola*, a strain presently classified as *Candida bombicola*. The prior art is also described in U.S. Pat. No. 3,445,337 and in Journal of the American Oil Chemistry Society, vol.65, no.9, September 1988, pp.1460–1466.

French patent application 2670798 also describes a process for the production of sophorolipids by fermentation with continuous supply or fed batch of esters of fatty acids or oils.

The sophorolipids obtained are considered as being a mixture of compounds represented by formulas (1) and (2), formula (1) representing the acid form and formula (2) the lactone form:

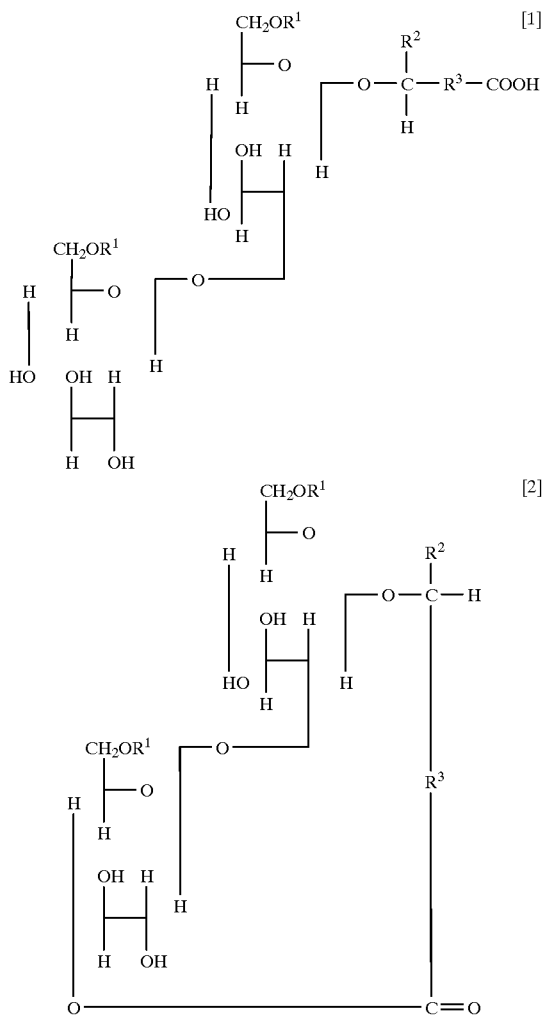

In these formulas, $R^1$ represents hydrogen or an acetyl group and $R^2$ hydrogen or an alkyl radical having 1 to 9 carbon atoms, when $R^3$ is a saturated hydrocarbon radical with 7 to 16 carbon atoms, or $R^2$ represents hydrogen or a methyl group, when $R^3$ is an unsaturated hydrocarbon radical with 13 to 17 carbon atoms.

Hitherto the preparation processes for products describe numerous homologues and the separation of one of the main forms (acid or lactone) e.g. requires extractions by alcohol (EP-B-209783), which are both long and expensive. Moreover, extraction by a specific solvent does not always give good results, because the solubility of all the homologues in a solvent can differ significantly, which affects the quality of the products obtained.

In addition, methanolysis reactions in the presence of an acid catalyst do not give better results and what is frequently obtained is a mixture of deacetylated esters or acids. The prior art (U.S. Pat. No. 4,197,166) also points out that it is extremely difficult to prepare by fermentation a desired product having a given homologue ratio.

Finally, it is known that the acetyl bonds in sophorolipids are chemically unstable and are very easily hydrolyzed by heating or prolonged storage close to neutrality or even at ambient temperature under slightly alkaline conditions, which leads to the obtaining of the completely deacetylated acid form. It is therefore extremely difficult by fermentation or chemistry to obtain a single product and a fortiori an acetylated product.

Moreover, in petroleum applications e.g. linked with the assisted recovery of petroleum, it is necessary to be able to create water-in-oil emulsions and therefore to be able to have emulsifying products which are more hydrophobic than hydrophilic, which cannot be the case of deacetylated acid products.

Therefore there is a demand in the industry for products having a fatty acid function and a saccharide structure with acetylated functions masking the very hydrophilic hydroxyl groups, particularly on products obtained by fermentation and incorporating a saccharide structure such as sophorose.

SUMMARY OF THE INVENTION

A process for the fed batch production of a sophorolipid composition incorporating a major part of at least partly acetylated acids under particularly advantageous conditions and obviating the aforementioned disadvantages has been discovered. More particularly, culturing takes place of at least one *Candida bombicola* or *Candida apicola* strain in a culture medium incorporating at least one sugar and at least one nitrogen source under appropriate conditions for producing said strain. The said strain is then exposed to a supply of an appropriate substrate under adequate aeration, temperature and pH conditions and the following sequence is performed at least once:

a) the strain is continuously supplied with said substrate at a supply rate in the reaction zone between 0.01 and 4 grams per hour and per liter of initial reaction volume and for a supply time such that the residual concentration of said substrate in the reaction zone is maintained at a value at the most equal to 18 grams per liter of initial reaction volume during said supply period;

b) the sophorolipid composition produced is recovered.

More specifically, the substrate consists essentially of at least one animal oil, at least one vegetable oil and at least one ester of said oil, said oils and said ester incorporating an aliphatic linear chain of 10 to 24 carbon atoms. In preferred manner, the continuous substrate supply can take place in accordance with a time-decreasing profile.

According to another feature of the process according to the invention, the stage of recovering the sophorolipid composition produced during the excretion stage comprises the separation of the strain from the fermentation liquid containing the sophorolipid composition, neutralization at a pH close to neutrality of the liquid and the elimination of the water by heating and under reduced pressure.

According to another variant, the recovery stage of the sophorolipid composition produced during the exretion stage comprises the separation of the strain from the fermentation liquid containing the sophorolipid composition and the elimination of the water under reduced pressure. This water elimination under reduced pressure preferably takes place by lyophilization.

The strain used is advantageously *Candida bombicola* CBS 6009. It can be obtained from a culture produced ex-situ or, according to another preferred variant, the strain contained in the culture medium can be directly exposed to a substrate supply. The observed productivity is then excellent and the sophorolipid yield is very good, e.g. at least 80 g/l of sophorolipids per liter of culture medium. The process can then be performed in the following way. Substrate is supplied by regulating the supply flow rate in the reaction zone under the operating conditions given hereinbefore, the substrate supply is stopped when the total injected substrate quantity reaches approximately at the most 280 g•l$^{-1}$ of initial reaction volume and the sophorolipid composition is recovered in the manner indicated hereinbefore.

According to another feature of the process and the continuous supply, the reaction zone can contain at the start of culture a substrate concentration of 0.5 to 40 g•l$^{-1}$ of initial reaction volume and advantageously 1 to 25 g•l$^{-1}$ and said strain is continuously supplied with substrate after a period of e.g. at the most 48 hours, i.e. when the substrate concentration is generally between 0.1 and 0.15 g•l$^{-1}$ and preferably between 0.1 and 5 g•l$^{-1}$ per liter of initial reaction medium.

According to another advantageous feature of the process making it possible to obtain good results, the continuous substrate supply rate to the reaction zone can be between 0.5 and 3.0, preferably between 1.0 and 2.5 and more specifically between 1.5 and 2.0 g•h$^{-1}$•l$^{-1}$.

Among the preferred oils and esters, reference can be made to the oil and ethyl or methyl esters of colza, sunflower, palm or soy oil. Excellent results were obtained with these esters and in particular an acetylated acid form selectivity of at least SOX, advantageously at least 60% and e.g. 70 to 90%.

The culture medium can comprise a mineral nitrogen source (in the form of ammonium ions) and/or organic nitrogen, e.g. in the form of urea and/or amino acids such as in particular yeast extract, soy peptone, casein hydrolyzates, maize macerating liquor, wheat gluten hydrolyzates and meat extracts. The addition of mineral elements such as e.g. potassium, sodium, magnesium and trace elements such as iron, manganese, molybdenum in the form of their salts (sulphates, phosphates, chlorides) can also make it possible to further improve growth.

The culture medium can comprise at least one sugar such as glucose or saccharose and optionally at least one ester described hereinbefore.

Advantageously, the sugar quantity added at the start of fermentation can be adjusted in such a way that the energy needs linked with the growth of the strain are covered, said growth being limited by a calculated nitrogen-containing source addition. For example, the sugar quantity can be 1 to 100 g/l based on the culture medium and preferably 20 to 80 g/l and more particularly 40 to 70 g/l. The nitrogen quantity is generally added as a function of the quantity of cells which it is wished to obtain.

The culture conditions are normally a temperature of 18 to 35° C. and a pH of 3.0 to 8.0. A good activity level was obtained at a temperature between 20 and 30° C. and a pH-range between 3.0 and 5.0 and excellent activity levels were observed at a temperature between 22 and 28° C. and a pH between 3.5 and 4.0. Fermentation is usually carried out under initial asepsis and aerobiosis conditions.

According to another feature of the process, it is possible to introduce the strain contained in the culture medium into the reaction zone in order to expose it to the substrate supply. However, according to another feature the strain can be removed from the culture medium by known methods and can be introduced into the reaction zone, where it is exposed to said substrate supply.

The sophorolipid production process is generally performed under the following conditions: temperature 18 to 35° C., pH 2.5 to 8.0, advantageously 3.0 to 4.0, aeration flow rate 0.2 to 2 v.v.m. under an absolute pressure of 1 to 5 bar and preferably 1 to 2 bar (1 bar=0.1 MPa).

Throughout the production period, the pH is controlled and regulated to a reference value in the range given hereinbefore by the addition of e.g. a potash or soda solution.

The quantity of cells used based on the initial reaction volume is normally 1 to 100 and preferably 10 to 30 g of dry weight per liter.

According to a particularly advantageous feature, at least one strain preculture stage can be performed prior to the culturing thereof in a preculture medium containing at least one nitrogen source and at least one carbon source chosen from within the group including at least one carbohydrate, at least one saturated or unsaturated fatty acid ester with 10 to 24 carbon atoms, at least one saturated or unsaturated aliphatic hydrocarbon with 10 to 20 carbon atoms, at least one aliphatic acid with 10 to 20 carbon atoms, at least one aliphatic alcohol with 10 to 20 carbon atoms and mixtures thereof, the carbohydrate proportion being at the most equal to 20% based on the preculture medium and the weight proportion of ester, hydrocarbon, alcohol and/or acid being at the most equal to 0.5%; and the culture medium is seeded with the preculture medium. In preferred manner, the preculture medium can comprise at least one carbohydrate and at least one other carbon source chosen from within the group including esters, hydrocarbons, alcohols and acids as defined hereinbefore.

According to another feature of the process, the preculture stage or stages can be performed at a temperature of 18 to 40° C., preferably 20 to 30° C., for a time period of 12 to 72 hours in each case and more particularly 24 to 36 hours.

According to another advantageous feature of the process the fatty acid ester, the aliphatic hydrocarbon, the aliphatic alcohol and the aliphatic acid can be in a weight proportion of 0.1 to 0.30% based on the preculture medium and the carbohydrate in a weight proportion of 2 to 12% based on the preculture medium. Particularly interesting results were obtained with a carbohydrate weight proportion of 6 to 10% in the preculture medium.

According to another advantageous feature of the process, the carbon source can be chosen from within the group incorporating said fatty acid esters with 16 to 18 carbon atoms, said hydrocarbons with 16 to 18 carbon atoms, said alcohols with 16 to 18 carbon atoms and said acids with 16 to 18 carbon atoms.

The nitrogen source used in the preculture stage is generally a mineral nitrogen source in the form of ammonium ions and/or organic nitrogen, as described hereinbefore for the culture medium.

The propagation of the strain generally takes place by seeding a preculture medium in small volume from a gelose-treated tube used for preserving said same strain.

Following an incubation period on a stirring or agitating table, said preculture medium is transferred into a production reactor, where the process can be carried out in accordance with the operating procedure described in French patent application EN 90/16211.

As a result of the process according to the invention, generally more than 55% of acid sophorolipids in acetylated form are obtained and preferably at least 60%, e.g. 60 to 70%. The performance of the preculture phase makes it possible to increase the selectivity.

The characterization of the structural forms of the sophorolipids is normally carried out by high performance liquid chromatography (HPLC) of the mixture obtained, equipped with an e.g. refractometric detector.

The acetylation level of the acid forms is generally determined by high performance liquid chromatography, equipped with an e.g. light diffusion detector.

EXAMPLE 1

The strain used is the yeast *Candida bombicola* CBS 6009, which is preserved by monthly subculturing on the gelose medium having the following composition:

| | |
|---|---|
| Peptic peptone (BIOMERIEUX Biothione) | 10 g/l |
| Yeast extract | 5 g/l |
| Colza ethyl ester | 15 g/l |
| Gelose | 30 g/l |

The propagation of the strain takes place on the following preculture medium:

| | |
|---|---|
| Glucose | 60 g/l |
| $(NH_4)_2SO_4$ | 4 g/l |
| $KH_2PO_4$ | 1 g/l |
| $MgSO_4, 7H_2O$ | 0.5 g/l |
| Dried maize macerating liquor | 5 g/l |
| Colza ethyl ester | 20 g/l |

For the preparation of this preculture medium, sterilization takes place together at 120° C. and for 25 minutes of the glucose, colza ethyl ester, $MgSO_4, 7H_2O$ in half the necessary water, while the $KH_2PO_4$, $(NH_4)_2SO_4$ and the maize macerating liquor are sterilized using the same sterilization means in the other half of the water. The preculture medium is reconstituted, following cooling to ambient temperature, by mixing the two solutions.

Seeding takes place in a 200 ml Erlenmeyer flask containing 30 ml of preculture medium. After incubating for 40 hours on the stirring table and at a temperature of 25° C., all the medium contained in the Erlenmeyer flask is transferred into a 2 liter Fernbach flask containing 200 ml of a medium, whose composition is identical to that of the Erlenmeyer flask. This second preculture stage is performed, like the first, under stirring at a temperature of 25° C. Fermentation takes place with the culture medium in a 4 liter reactor containing a 2 liter reaction volume. The medium is stirred or agitated by a Rayneri turbine, having a rotation speed fixed at 1000 r.p.m. Aeration is 0.5 v.v.m. of air under atmospheric pressure. The culture medium has the same composition as that used for the preculture chain with the exception of the colza ethyl ester which is added continuously, as from seeding, at a supply rate of 1.5 g/h/l of medium.

Seeding of the reactor takes place with the entire contents of the Fernbach flask. Following auto-acidification of the culture, the pH of the medium is kept constant at 3.5 by adding 4 N soda control led by means of an electrovalve dependent on a pH-meter.

Culturing lasts 144 hours. The strain growth phase lasts approximately 24 hours and at the end of this period the glucose is exhausted and the substrate is then constituted by the colza ethyl ester supplied in continuous manner. At the end of fermentation, the yeast strain cells are eliminated by centrifuging and the liquid phase is lyophilized. Thus, per liter of medium, recovery takes place of 116 g of a solid containing 102 g of sophorolipids. Analysis of the structural forms of the sophorolipids takes place by high performance liquid chromatography (HPLC) using a HYPERSIL C-18 column with a length of 15 cm (Interchim, Montluçon. France) and a refractometric detector. The solvent used for elution is a mixture of acetonitrile and water in a ratio 70:30 (vol/vol) at a rate of 0.7 ml/min. The acid forms of the acetylated or non-acetylated sophorolipids are eluted at the head, followed by the lactone forms. In order to determine the acetylation rate of the acid forms, use is made of HPLC equipped with a column identical to that referred to hereinbefore and a light diffusion detector. The resolution of the acid forms is obtained with an acetonitrile/water elution gradient. The eluent mixture contains 98% water at the start of analysis. The intervention of the linear gradient brings the eluent composition to 30% water after 48 minutes. The composition of the mixture is then kept constant for an additional 14 minutes. Thus, determination takes place that the mixture of the sophorolipids is constituted by 88 g/l of acid forms (i.e. 86.2% of the total sophorolipids) and that among them the acetylated forms represent 77 g per liter of the initial culture medium (i.e. 87% of the total acid forms). The yield of the acid forms of sophorolipids based on the two carbon sources, glucose and colza ester, is 31.8%.

EXAMPLE 2

(Comparative with Respect to Example 1)

Example 1 is repeated and during the excretion phase there are 4 additions of glucose in solid form, each of them being equal to 50 g/l of medium. These additions respectively take place after 24, 48, 72 and 96 culture hours. Under these conditions 255 g/l (quantity based on the initial volume) are obtained of a solid containing 241 g/l of sophorolipids. The acid forms represent 71 g/l (30.7% of the total sophorolipids) and among them the acetylated forms are 56 g/l (79% of the acid forms). The acid forms sophorolipid yield based on the two carbon sources, glucose and colza ester, is 14.9%.

EXAMPLE 3

Example 1 is repeated, but reducing the colza ethyl ester quantity used in the two preculture stages from 20 to 2 g/l. Under these conditions 115 g/l (quantity based on the initial volume) are obtained of a solid containing 99 g/l of sophorolipids. The acid forms represent 89 g/l thereof (90% of the total sophorolipids) and among these the acetylated forms represent 78 g/l (87% of the acid forms). The acid forms sophorolipid yield based on the two carbon sources, glucose and colza ester, is 32.2%.

EXAMPLE 4

Example 1 is repeated replacing the colza ethyl ester by sunflower methyl ester. At the end of the test 114 g/l of a solid are obtained containing 98 g/l of sophorolipids. The quantity of acid form sophorolipids is 84 g/l of (i.e. 85% of the total sophorolipids), including 74 g/l of acetylated acids (i.e. 88% of the acid forms). The acid forms sophorolipid yield based on the two carbon sources, glucose and colza ester, is 30.4%.

EXAMPLE 5

Example 1 is repeated, while increasing the colza ethyl ester injection rate from 1.5 to 1.9 g/l. At the end of the test 137 g/l of a solid are obtained, which contain 120 g/l of sophorolipids. The acid forms represent 97 g/l thereof (80% of the total sophorolipids), including 82 g/l of acetylated acids (84% of the total acids). The acid forms sophorolipid yield based on the two carbon sources, glucose and colza ester, is 41.0%.

We claim:

1. A process for the fed batch production of a sophorolipid composition comprising culturing *Candida bombicola* CBS 6009 strain in a culture medium incorporating a sugar and a nitrogen source under effective conditions for producing said strain and, thereafter, exposing said cultured strain in a reaction zone to a supply of a substrate under adequate aeration, temperature and pH conditions, said substance consisting essentially of at least one animal oil, at least one vegetable oil, and/or at least one ester of said oil, said oils and said ester incorporating an aliphatic linear chain with 10 to 24 carbon atoms, and wherein the following sequence is performed at least once:

(a) continuously supplying the substrate to the strain culture at a flow rate in the reaction zone between 0.01 and 4 grams per hour and per liter of initial volume and for a supply time such that the residual concentration of said substrate in the reaction zone is maintained at a value at the most equal to 18 grams per liter of initial reaction volume during said supply time and producing the sophorolipids while said reaction zone is essentially free of sugar during at least part of said supply time, and (b) recovering the resultant sophorolipid composition having an acetylated acid form of at least 50% compared to other forms of sophorolipids.

2. A process according to claim 1, wherein the sophorolipid composition recovery stage comprises the separation of the strain from the fermentation liquid containing the sophorolipid composition, neutralization at a pH close to neutrality of the liquid and the elimination of the water by heating and under reduced pressure.

3. A process according to claim 1, wherein the sophorolipid composition recovery stage comprises the separation of the strain from the fermentation liquid containing the sophorolipid composition and the elimination of the water under reduced pressure.

4. A process according to claim 1, wherein the substrate supply is stopped when the total quantity of injected substrate reaches at the most 280 $g \cdot l^{-1}$ of initial reaction volume.

5. A process according to claim 1, wherein the sophorolipids are produced at a temperature of 18 to 35° C., a pH of 2.5 to 8, and wherein the reaction zone is aerated at a rate of 0.2 to 2 v.v.m. under a pressure of 1 to 5 bar.

6. A process according to claim 1, wherein the substrate consists of at least one colza, sunflower, palm and/or soy oil and at least one ester of said oils.

7. A process according to claim 1, wherein the substrate flow rate in the reaction zone is between 1.0 and 3.0 $g \cdot l^{-1} \cdot h^{-1}$ of initial reaction volume.

8. A process according to claim 1, wherein the strain comes from a culture produced ex-situ.

9. A process according to claim 1, wherein the strain contained in the culture medium is exposed to the substrate supply.

10. Process according to claim 1, wherein the reaction zone contains at the start of culturing a substrate concentration of 0.5 to 40 $g \cdot l^{-1}$ of initial reaction volume and said strain is continuously supplied with substrate when the initial substrate concentration is 0.1 to 15 $g \cdot l^{-1}$.

11. A process according to claim 1, wherein the quantity of cells used based on the reaction volume is 1 to 100 g of dry weight per liter.

12. A process according to claim 1, wherein, prior to the culturing stage, at least one preculturing stage of the strain is performed under appropriate preculture conditions in a preculture medium containing at least one nitrogen source and at least one carbon source chosen from within the group incorporating at least one carbohydrate, at least one saturated or unsaturated fatty acid ester with 10 to 24 carbon atoms, at least one saturated or unsaturated aliphatic hydrocarbon with 10 to 20 carbon atoms, at least one aliphatic alcohol with 10 to 20 carbon atoms, at least one aliphatic acid with 10 to 20 carbon atoms and mixtures thereof, the carbohydrate proportion being at the most equal to 20% and preferably between 2 and 12% based on the preculture medium and the weight proportion of ester, hydrocarbon, alcohol and/or acid is below 0.5%, preferably between 0.1 and 0.3%, based on the preculture medium and the culture medium is seeded with the preculture medium.

13. A process according to claim 12, wherein the preculture medium comprises as the carbon source a carbohydrate and at least one other carbon source chosen from the group consisting of esters, hydrocarbons, alcohols and acids of claim 12.

14. A process according to claim 1, wherein the sophorolipid comprises at least 60% of the acetylated acid form.

15. A process according to claim 1, wherein the sophorolipid comprises at least 70–90% of the acetylated acid form.

16. A process according to claim 1, wherein the sophorolipids are produced while said reaction zone is essentially free of sugar during most of the supply time.

17. A process according to claim 1, wherein the sugar is glucose.

18. A process according to claim 16, wherein the sugar is glucose.

* * * * *